(12) United States Patent
Wittmann

(10) Patent No.: US 7,662,169 B2
(45) Date of Patent: Feb. 16, 2010

(54) PROSTHESIS AND METHOD FOR LOWERING ABDOMINAL PRESSURE

(76) Inventor: Dietmar H. Wittmann, 990 Gulf Winds Way, Nokomis, FL (US) 34275

( * ) Notice: Subject to any disclaimer, the term of this patent is extended or adjusted under 35 U.S.C. 154(b) by 668 days.

(21) Appl. No.: 10/636,728

(22) Filed: Jul. 13, 2004

(65) Prior Publication Data

US 2004/0221431 A1  Nov. 11, 2004

(51) Int. Cl.
*A61B 17/08* (2006.01)
*A61B 17/50* (2006.01)

(52) U.S. Cl. ........................ 606/216; 606/215
(58) Field of Classification Search ........... 606/216, 606/215, 212, 213
See application file for complete search history.

(56) References Cited

U.S. PATENT DOCUMENTS

| | | | |
|---|---|---|---|
| 4,112,947 A | 9/1978 | Nehring | |
| 4,382,441 A | 5/1983 | Svedman | |
| 4,452,245 A | 6/1984 | Usher | |
| 4,569,674 A | 2/1986 | Phillips et al. | |
| 4,655,754 A | 4/1987 | Richmond et al. | |
| 4,969,880 A | 11/1990 | Zamierowski | |
| 5,636,643 A | 6/1997 | Argenta et al. | |
| 5,645,081 A | 7/1997 | Argenta et al. | |
| 5,893,368 A | 4/1999 | Sugerman | |
| 6,039,741 A * | 3/2000 | Meislin | 606/72 |
| 6,071,304 A | 6/2000 | Augustine et al. | |
| 6,725,794 B2 | 4/2004 | Usa | |
| 6,855,135 B2 | 2/2005 | Lockwood et al. | |

OTHER PUBLICATIONS

A. L. A L Valenta, Using the Vacuum Dressing Alternative for Difficult Wounds, American Journal of Nursing, Apr. 1994, pp. 44-45.
M.G. Dunlop et la., Vacuum Drainage of Groin Wounds After Vascular Surgery: a controlled trial, Br. J. Surg. May 1990, pp. 562-583 , vol. 77.
J.W.Saunders, Negative Pressure Device for Controlled Hypotension During Surgical Operations, the Lancet, Jun. 1952, pp. 1286-1287.
D. H. Wittmann et al., The Abdominal Compartment Syndrome, Journal of the American College of Surgeons, Jun. 1995, pp. 745-753, vol. 180.
R Miller et al., Late Fascia Closure in Lieu of Ventral Hernia, The Journal of Trauma, Nov 2002, pp. 843-849, vol. 53 No. 5.

* cited by examiner

*Primary Examiner*—Vy Q. Bui
(74) *Attorney, Agent, or Firm*—Frijouf, Rust & Pyle, P.A.

(57) ABSTRACT

A two-sheet fascial expander prosthesis for temporary use and method of using it to treat abdominal hypertension and associated organ system function impairment, in which each flat sheet is attached to the fascia only at opposite sides of an incision. One side of each sheet is armed with mating fastening elements that bond when united to bring about high tensile shear strength and low tensile peeling-off resistance permitting easy separation for diagnostic and therapeutic abdominal entry. The invention is useful because it expands the fascia and adds compliance to the envelope of the abdominal cavity by bridging the gap between free borders of the incised fascia containing intra-abdominal organs without strangulating their blood supply and retaining some tension on the fascia to prevent retraction and bringing the edges closer together as healing progresses, and permitting final removal of the patch and fascia-to-fascia closure. The method of producing and testing biocompatibility of the two-sheet fascia prosthesis also is disclosed.

2 Claims, 7 Drawing Sheets

# PROSTHESIS AND METHOD FOR LOWERING ABDOMINAL PRESSURE

CROSS-REFERENCE TO RELATED APPLICATIONS

Related U.S. Application Data

This application claims priority based on Provisional Patent Application No. 60/230,202 filed Sep. 5, 2000.

| U.S. Pat. Document 5,893,368 | Apr. 13, 1999 | Sugerman | 128/898; 601/11; 606/119 |
|---|---|---|---|
| U.S. Pat. Document 6,039,741 | Mar. 21, 2000 | Meislin | 606/72 |
| U.S. Pat. Document 4,452,245 | Jun. 5, 1984 | Usher | 128/334 R |

STATEMENT REGARDING FEDERALLY SPONSORED RESEARCH

Not applicable

REFERENCE TO A "MICROFICHE APPENDIX"

Not applicable

BACKGROUND (1) Field of the Invention

This invention relates to decompression of abdominal compartment syndrome with devices and the method of using and establishing biocompatibility for such devices.

More particularly it relates to reversing organ function impairment, venous and arterial perfusion impairment and avoiding diminishing death rates from increased intra-abdominal pressure and abdominal compartment syndrome, by adding compliance to the envelope (fascia) that surrounds the abdominal cavity and preventing huge abdominal incisional hernias. The device is usually removed after organ function is restored when abdominal pressure has normalized and the fascia can be sutured by traditional techniques.

(2) Description of Related Art

Increased intra-abdominal pressure or abdominal hypertension from any cause occurring acutely may lead to abdominal compartment syndrome, because the abdominal cavity with its content is contained within an envelope of limited compliance. Abdominal compartment syndrome impairs functions of vital organ systems in humans and animals. With sustained abdominal hypertension above a critical value high mortality rates are observed, which depends on preexisting diseases and physiological resources of the patient.

Therapy of abdominal hypertension is most effectively accomplished by incising the envelope of the abdominal cavity sufficiently to free intra-abdominal organs from their engorgement to protrude through the incision a process that is called decompression. The critical structure of the abdominal envelope is the abdominal fascia; a sheet of fibrous tissue that lies deep to the skin and forms an investment of abdominal organs. The abdominal fascia has limited compliance and increased intra-abdominal volume translates directly into pressure increases and beyond a certain threshold, blood flow to all structures within the envelope is strangulated.

Diminished blood flow to vital organs leads to tissue hypoxia and sequential organs system dysfunction and, if not treated, to death. The first publication about renal function impairment in the presence of abdominal hypertension was published in 1876, by E C Wendt (Arch. Heilkunde. 1876; 17:527), but clinicians did not fully appreciate the condition and only recently began treating abdominal hypertension by leaving the abdomen open or provisionally covering the exposed organs with any fabric including infusion bags and as meshes described in U.S. Pat. No. 4,452,245 (Schein, et al, J Am Coll Surg 180:745-753, 1995). Sugerman developed an external device to treat increased intra-abdominal pressure (U.S. Pat. No. 5,839,368).

Leaving the abdomen open is associated with high mortality rates, fistula formation, and large incisional hernias. Using available meshes (U.S. Pat. No. 4,452,245) to bridge the gap between fascias is associated with similarly high complications and mortality rates. In a recent publication the open abdomen technique is still advocated as the treatment of choice for abdominal compartment syndrome. (Miller, P R, J. Trauma 53:843-849, November 2002) The authors observed high intra-abdominal pressures and abdominal compartment syndrome from visceral edema in 122 of 646 patients who underwent laparotomy for trauma, and the abdomen of these 122 patients was left open after incising the fascia. More than 40% died. The authors presented a method of "late fascia closure in lieu of ventral hernia" and had to accept a high hernia rate nevertheless.

There are other conditions when operative manipulations, excessive fluid resuscitation induce massive peritoneal edema increasing intra-abdominal volume while the surgeon is operating. Closing the abdomen forcefully in such situations over increased intra-abdominal volumes will increase intra-abdominal pressure, and lead to multi-system organ failure and death.

Traditionally, the surgeon was always closing the abdomen by suturing the fascia. The need to treat increased intra-abdominal volumes to prevent abdominal compartment syndrome and multi-organ dysfunction was traditionally neglected until very recently when the term "abdominal compartment syndrome" was recognized as a separate clinical entity (Schein, M. et al, J Am Coll Surg, 180; 745-753, 1995).

Upon recognition of the clinical importance of sustained acute increases in intra-abdominal volume and pressure surgeons started just leaving the abdomen open for treatment and this technique remains the standard of care as mentioned above. Leaving the abdomen open invariably is followed by said complications. In an attempt to reduce complications other devices such as plastic meshes were used to act as fascial prostheses covering exposed abdominal organs. Plastic meshes, however, need to be reopened and often replaced for abdominal re-entry. Re-uniting the fasciae is rarely possible using prior art devices and high rates of abdominal hernias develop in most cases even when meshes are used to cover the open abdomen.

As treatment progresses and edema lessens most of the prior art devices cannot accommodate decreases in abdominal distention and have to be replaced by a similar member and resutured.

There is obviously a need for fascial prosthesis that expands the abdominal envelope temporarily by adding compliance to accommodate the expanded abdominal organs and structures as long as the abdominal volume increase prevails. This device should also prevent the fasciae from retracting sideways to be able to reunite them for final regular fascia-to-fascia suture when abdominal pressure has normalized without leaving foreign material in situ at the same time.

There is also a need for a method and device that reduces high mortality rates and high rates of hernia and fistula formation in patients who require treatment for abdominal hypertension reversing organ function impairment, venous and arterial perfusion impairment and abdominal compartment syndrome. The device is usually removed after organ function is restored when abdominal pressure has normalized and the fascia can be sutured by traditional techniques.

More precisely a need exists for a simple, effective, improved method and use of device use for decompressing abdominal hypertension for protecting exposed abdominal organs, for opening and closing incisions without tissue damage, for permitting final fascial closure without leaving a foreign body in place, and for averting complications including infectious risks during the entire process.

BRIEF SUMMARY OF THE INVENTION

The objects of the present invention are to provide a simple, effective, and improved method and fascial prosthesis device for decompressing increased abdominal pressure, bridging fascial gaps, protecting abdominal contents, temporary closing the incision so that it can be subsequently opened and re-closed as needed, and finally closing the abdomen fascia to fascia without need for prosthetic material and preventing bacterial contamination during the decompression and reclosure period at the same time.

The device of the present invention basically comprises two flexible, trimmable sterile sheets. The first flexible, trimmable sheet has a relatively smooth bottom for covering exposed intraabdominal organs, and a top surface, which will mate with or form a cohesive, releasable bond with the bottom surface of the second, flexible, trimmable sheet.

In the preferred embodiment, the kit consists of a sterile package containing two sterile rectangular sheets of plastic Velcro-like material, each about 20×40 cm. One sheet is characterized by having "hooks" of various shapes on the bottom, while the other sheet has a top with "loops" to which the "hooks" attach when the two pieces are placed one upon the other with the "hooks" on the "loops". The "hooks" are not hooks in the classical sense. They consist of micromushrooms, or triangular, or semicircular structures with one open end which functionally act as hooks. Triangular and semicircular structures with one open end and structures of any other configuration may also be used as long as the structures provide the closing mechanism of said fascial expander prosthesis. Once the sheets are joint the united sheets can only be disconnected by lifting vertically and separating one sheet from the other (vertical pull). They cannot be separated by tangentially pulling the sheets apart (tangential pull).

In the methods of the present invention, one edge of the first sheet (loop sheet) is attached with the top of the sheet with its mating surface with loops facing upward, and the relatively smooth bottom facing downward. The loop sheet is sutured to the fascia and the free end is inserted between the opposite parietal peritoneum and the intestines so that the first sheet protects any exposed abdominal contents. The second flexible, trimmable sheet (hook sheet) is then similarly sutured to the opposite fascia of the abdominal wound with the bottom-mating surface of hook structures facing downward. To temporarily close the wound a slight pulling is exerted on each of the two sheets to put the fascia under minimal tension, and the mating surfaces are brought together to close the incision. Intra-abdominal organs may be protected during the process by covering the mating surfaces of the second sheet with a towel, as long as the abdomen is open.

Subsequently, when the abdominal re-exploration is performed, the bonds between the mating surfaces are broken and the sheets folded back to open the previously closed incision. If the wound is to be again temporarily closed, the process is reversed taking care to insure that both abdominal wall fasciae are again under minimal tension so that they do not retract. If, when the prosthesis is reclosed, and the edges of the fasciae be pulled closer together than during the previous abdominal entry, the sheets can be tailored to the proper size by trimming them with scissors to an equivalent size to the distance between the opposed fascial edges and the excess material removed. The opening and closing can be repeated until the abdomen is ready to be permanently closed at which time the remainders of the two sheets are removed and the incised ends of the fascia joined by a continuous suture or other traditional fascia closing technique. During the entire procedure that may last several days, the abdominal opening with the fascial prosthesis is protected from becoming contaminated by applying a self-adhesive plastic sheet cover onto a 20 cm skin area that surrounds the abdominal opening. To collect accumulating peritoneal fluid from the abdominal cavity above said prosthesis and underneath the self-adhesive plastic sheet, negative pressure is applied using a drain and an external suction pump. The combination of the two hermetically seals the abdominal aperture.

The novel method of the present invention is simple to handle and cost effective as it better uses hospital resources and reduces both mortality and morbidity by decompression of the abdominal compartment syndrome. Decompression is achieved by temporarily adding compliance to the abdominal envelope (abdominal fascia) to terminate strangulation of intra-abdominal organs and vessels. Decompression reverses multi system organ dysfunction and impairment of venous and arterial blood flow from sustained abdominal hypertension.

The novel method is also advantageous, because it permits stepwise re-approximation of the natural fascial edges to allow removal of the device and final traditional fascial closure with sutures. Even after many abdominal entries the abdomen looks eventually like having undergone only one single operation with one single scar.

Without said fascial expander prosthesis fascias on both sides of the abdominal aperture would retract laterally resulting in permanent huge abdominal hernias that disable the patient. Said prosthesis prevents hernia formation.

Without said fascial expander prosthesis bowel would be exposed to atmospheric pressures without any counter pressure. In the closed abdomen that has not been opened the abdominal envelope exerts some pressure naturally. Higher bowel perforation and fistula rates are seen when bowel that is friable from inflammation and bowel distension is exposed to lower atmospheric pressure. Fistula formation is greatly reduced when said prosthetic device is used to provide tailored pressure from the outside.

It will be apparent to those skilled in the art that the present invention fulfills the above-stated objectives and also provides other advantages.

BRIEF DESCRIPTIONS OF THE SEVERAL VIEWS OF THE DRAWINGS

FIG. 3.D shows the abdominal wall with the fascial expander prosthesis removed and fascia closed.

DETAILED DESCRIPTION OF THE INVENTION

Description of Preferred Embodiment

Figure 1:
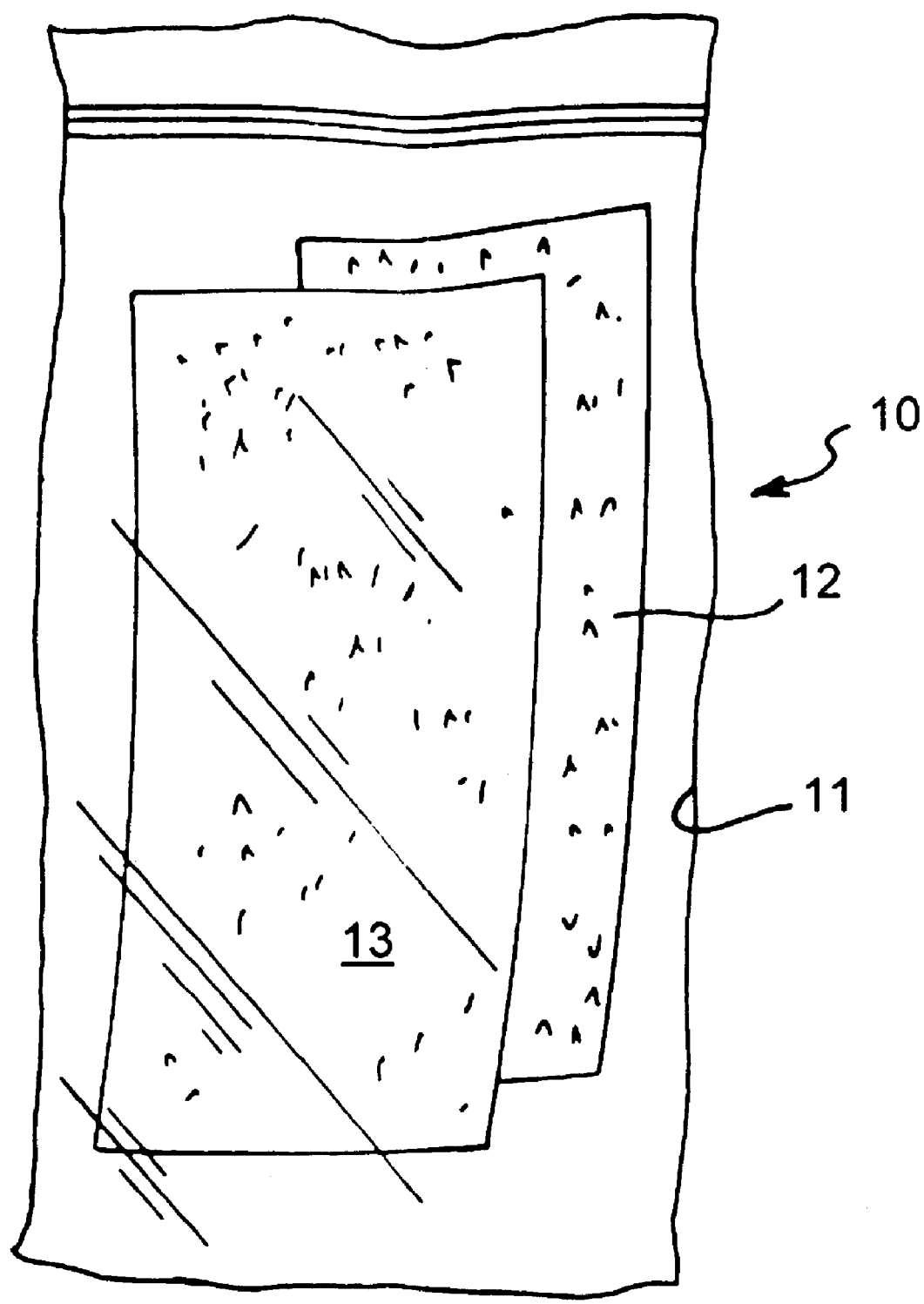
FIG. 1 is a perspective view of a kit of the present invention.
Figure 2:
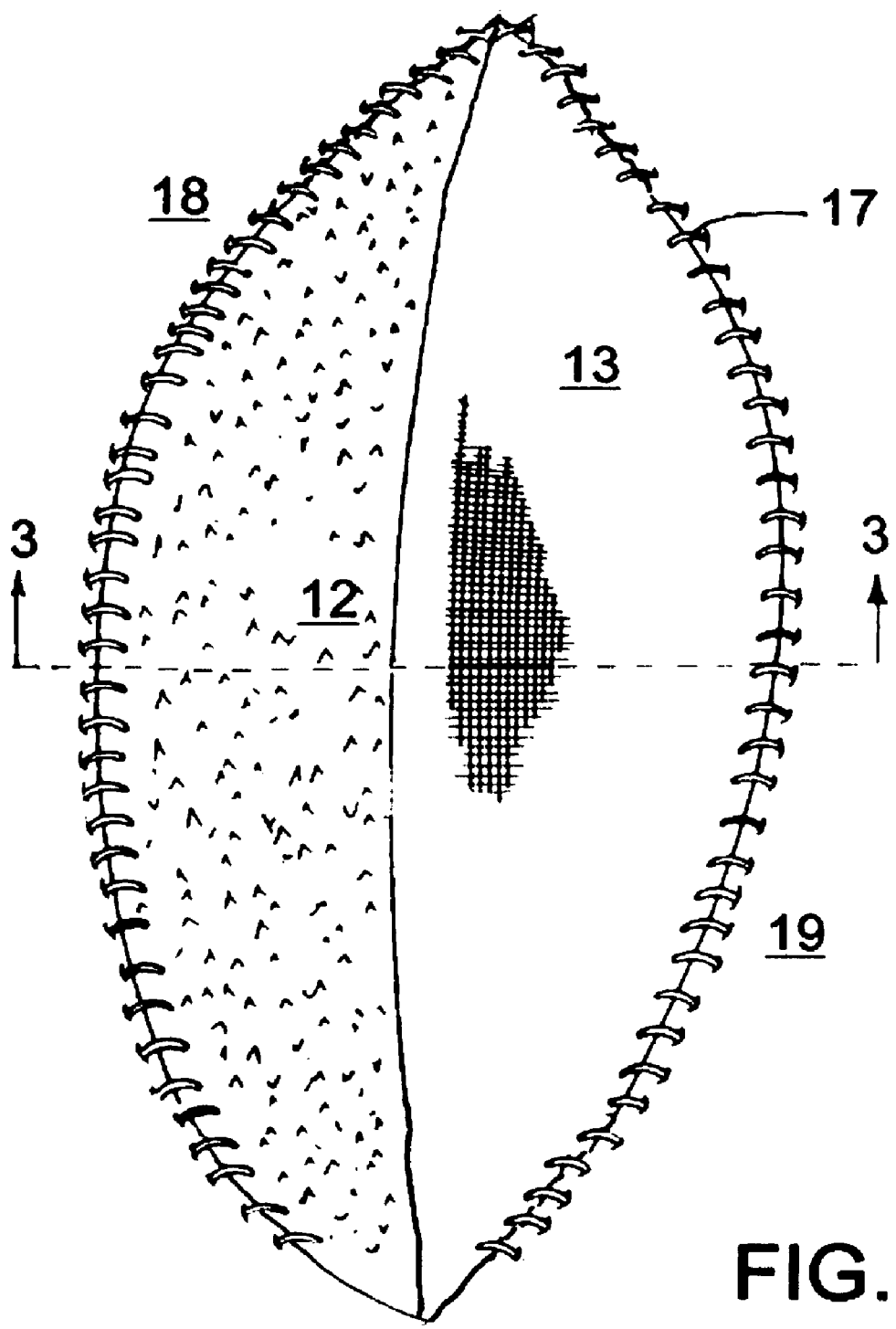
FIG. 2 is a perspective view showing the present invention closing an abdominal incision.

In the preferred embodiment of the invention shown in FIG. 1, the prosthesis, or device 10 is stored in a sealed outer package 11 with a sterile interior which contains a sterile loop sheet 12 and a sterile hook sheet of micromushrooms or other hook like structures 13.

Figure 3:
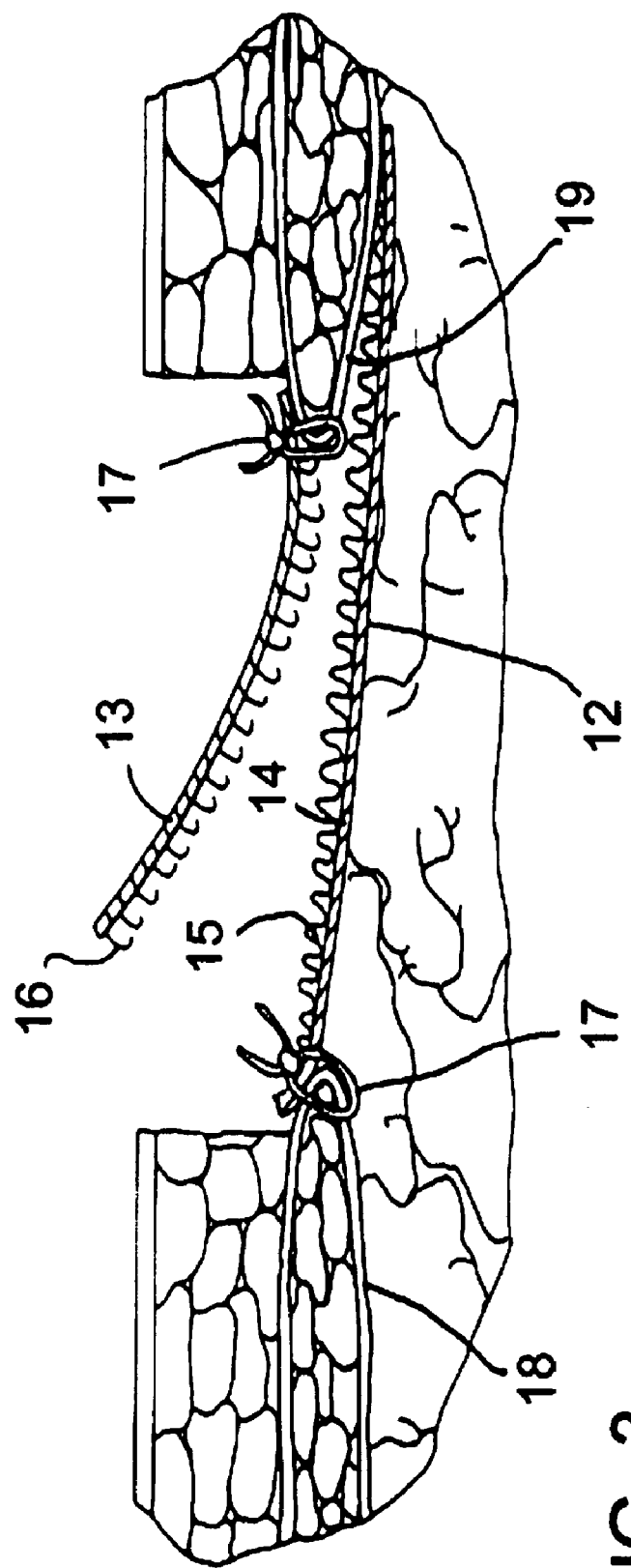
FIG. 3 is a view taken along lines 3-3 in FIG. 2.
Figure 4:
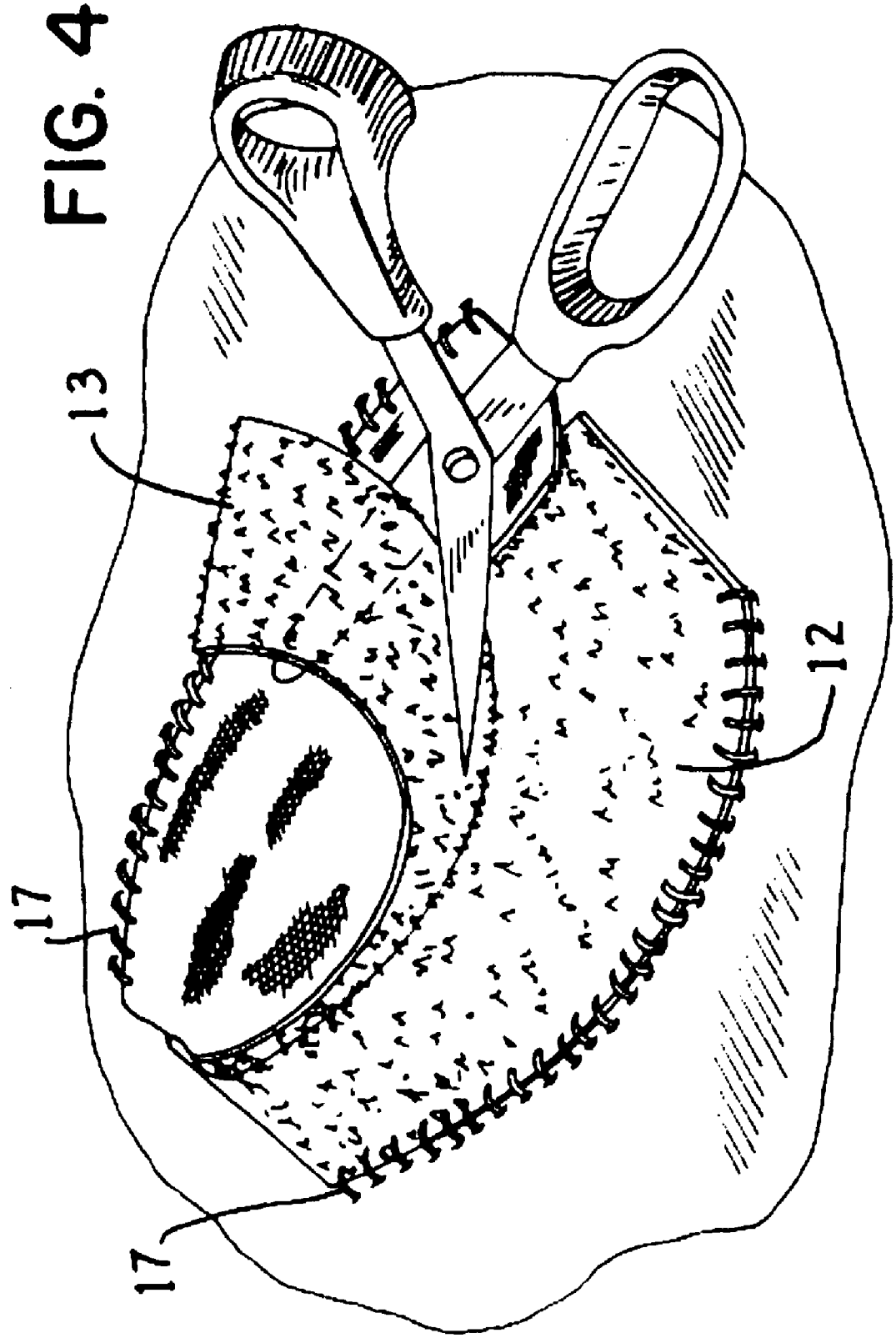
FIG. 4 is another view like FIG. 2 showing the device of the invention being trimmed with scissors to remove excess material.
Figure 5:
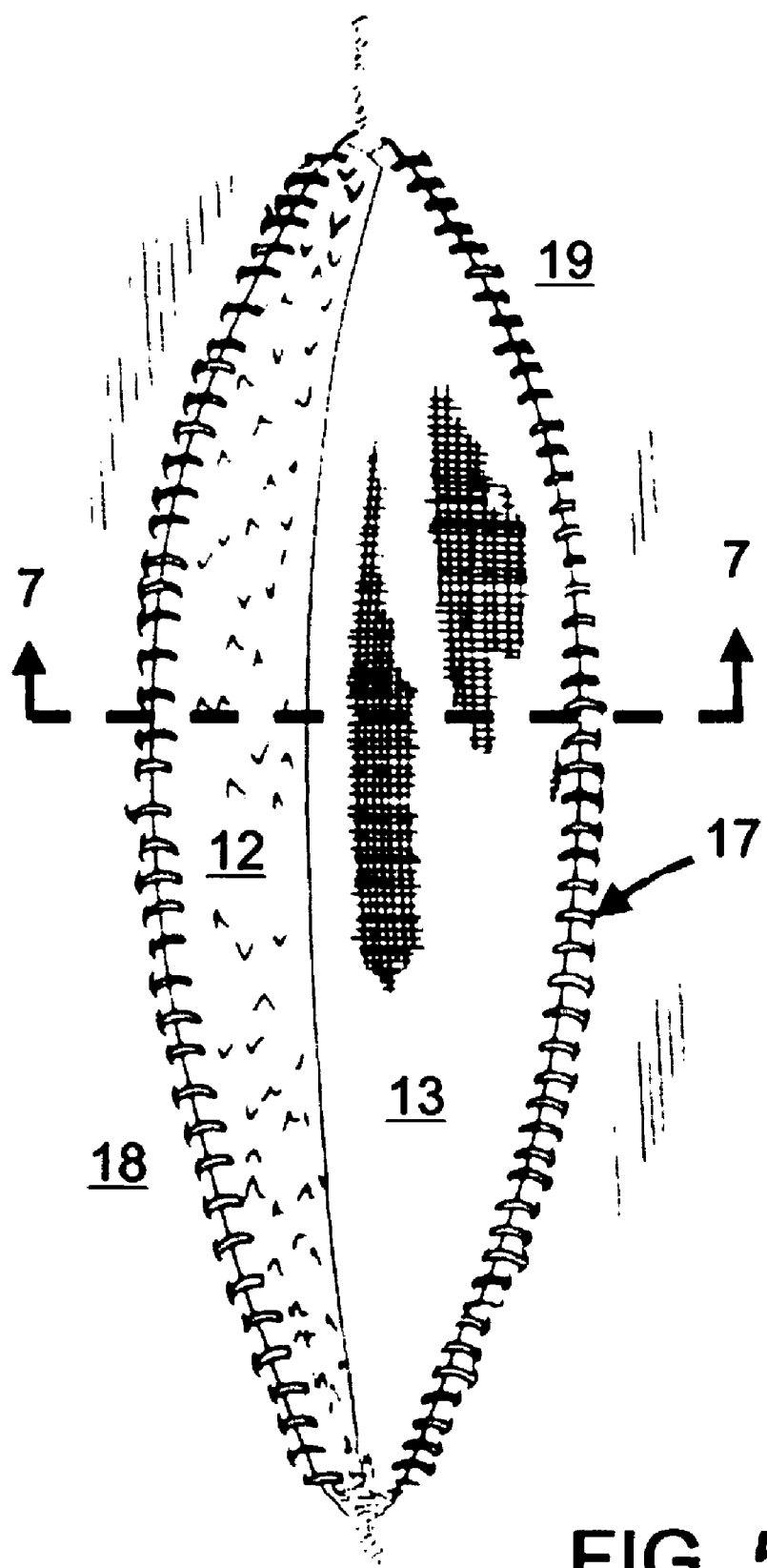
FIG. 5 is a view like FIG. 2 showing the abdominal incision closed after trimming; and, FIG. 6 is a view similar to FIG. 3 showing the final stage of applying a protective cover to avert exogenous contamination.
Figure 6:
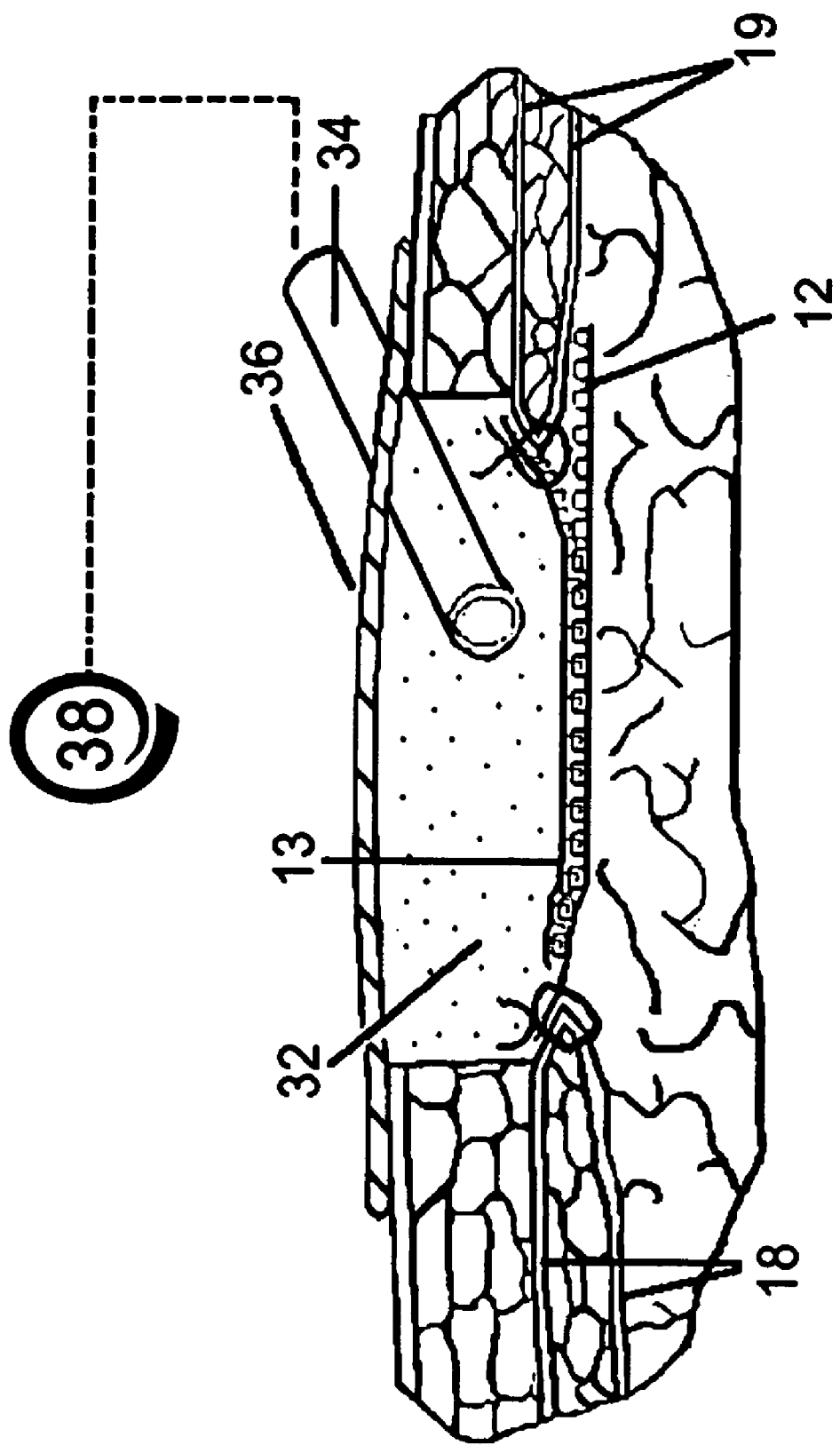

As seen in FIG. 3, the sheet 12, has a smooth bottom 14, and a top 15 consisting of multiple spaced filamentous looped anchors ("loops") rooted on said sheet, which is adapted to mate with the bottom 16, of the male sheet 13. Sheets 12 and 13 mate. The top 15, of the female sheet 12, is covered with "loops" and the bottom 16, of the male sheet 13, is provided with a multitude of "hook-like" protuberances (micromushrooms) that mate 15 with the looped surface to releasable bond the sheets 12 and 13 together.

The sheets 12 and 13 should be made of a biocompatible, easily sterilized fabric, which can be easily and securely sutured, and easily trimmed using conventional operating room instruments. Preferably, the sheets 12 and 13 are of a polyester material. The loop sheet 12 is made of a 20 polymer and the hook sheet 13 is made of a polymer, polypropylene, polyurethane and polyacrylate or biocompatible polypropylene only.

The preferred method of using the device or temporary implant of the present invention will be described in conjunction with FIGS. 2 to 5.

When it is desired to bridge the gap of an fascial incision, as for example at the end of an abdominal entry, one edge of the loop sheet 12, is attached with a running suture 17, to one fascia 18 with the top or loop side 15 up, i.e. so that the smooth bottom side of the loop sheet does contact bowel wall, omentum, or other intraperitoneal organs. The smooth biocompatible bottom of the loop sheet 12 protects the exposed abdominal contents. The free end of the loop sheet that results from discrepancy between the smaller fascial opening and the bigger size of the loop sheet is inserted between the parietal peritoneum and the intestines at the opposite edge of the incision.

One edge of the hook sheet 13, which is preferably of a contrasting color, is similarly sutured to the opposite fascia 19 so that the bottom or hook side 16 will face toward the loop side 15 of sheet 12, which is covering the abdominal organs. Then the fascial edges are approximated by pulling the free edges of both of the sheets 12 and 13 toward each other to exert a minimal positive tension on the fascia and the cohesive surfaces are mated to close the incision and make a temporary abdominal closure.

In FIG. 3, the sheets 12 and 13 can be seen overlapped and ready to be bonded together by the mating of the hook top 15 and bottom 16. When thus mated the sheets 12 and 13 cannot be separated (by tangential pull) except by lifting the male sheet 13 off the female sheet 12 (vertical pull).

Gauze 32 is utilized to cover the hook sheet 12 and subcutaneous tissue up to the level of the skin. A suction drain tube 34 is imbedded into the gauze 32. Following this, a plastic drape 36 having an adhesive side is applied to the skin to cover the entire abdominal wall and the chamber above the prosthesis, leaving a tunnel for the drain tube. This seals the abdominal cavity and keeps it sterile. The area of the skin covered by the plastic drape 36 should cover a distance of at least 20 cm from any edge of the abdominal wound. This plastic drape seals off the abdominal cavity and suction is applied to the drain tube 32 by a pump 38 to provide a sealing negative pressure and to collect abdominal fluid for measurement of protein losses and other factors for possible replacement.

The interval between two operations of a series of planned abdominal re-entries or staged abdominal repairs should not exceed thirty six hours after the completion of the previous abdominal entry. It is important to permanently close the abdomen by suturing the fascia as early as possible when most of the peritoneal edema has disappeared. With every abdominal reentry the fascial edges should be pulled closer together to decrease the gap between the fascias.

Figure 7:
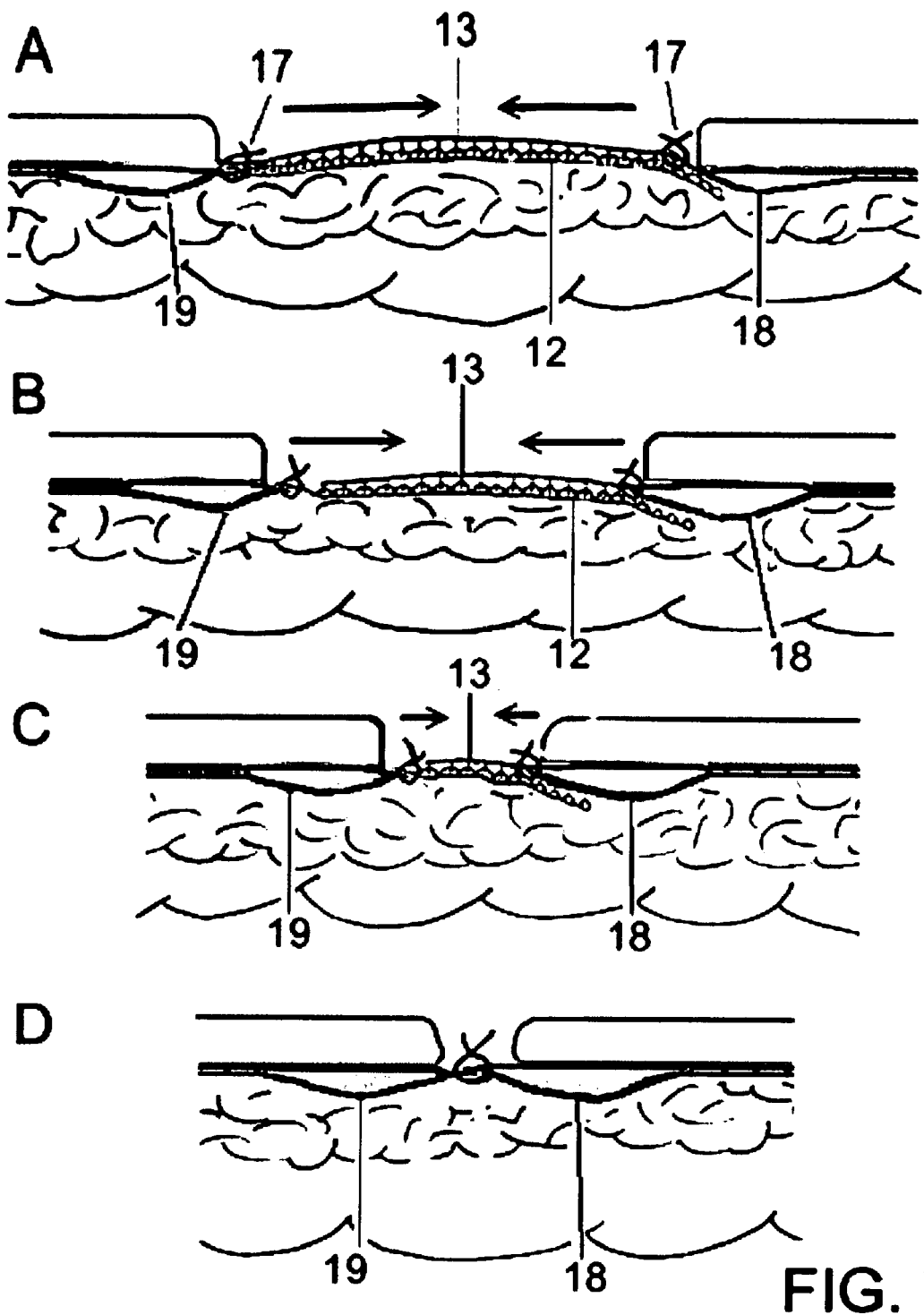
FIG. 7 shows 4 views like FIG. 3 with the female and mal sheets united at various stages of abdominal hypertension.

The abdominal cavity can permanently be closed once the problem within the abdominal cavity bringing about abdominal hypertension is solved. The sheets 12 and 13 are removed by taking out the running sutures. The hook sheet 13 is first removed from one side and then the loop sheet 12 from the other side. Subsequent to this, the fascia is closed by conventional suture technique. In FIG. 7 various closing stages are shown to demonstrate the technique of decreasing the size of the abdominal opening and size of the fascial expander prostheses by successively trimming off excessive material during subsequent abdominal entries and by re-approximating the fascial edges until the fascias are close enough to permit removal of said prosthesis and traditional permanent fascial closure.

The device 10 incorporating sheets 12 and 13 must be compatible for use in abdominal surgery. For that purpose, the sheets 12 and 13 of hook and loop material are cut to a predetermined size to accommodate the largest of sizes of expected incisions and are measured for compliance. The sheets are easily trimmed to a smaller size at the time of surgery.

The sheets are tested to confirm biocompatibility by testing methods required by the FDA for use in humans. For this purpose a battery of tests is performed to rule out any harm to human tissue including cytotoxicity.

The components are packaged in an internally sterile package such as a transparent plastic bag for storage until use.

What I claim as my invention is:

1. A process for bridging a gap of an abdominal incision, the abdominal incision traversing through a skin layer of a living organism for exposing abdominal organs, the abdominal incision defining a first edge and an opposite edge, an enlarged abdominal volume causing an abdominal hypertension and protruding of the abdominal organs through the abdominal incision, the enlarged abdominal volume of the abdominal organ resisting the first edge and the opposite edge from mating together, the process comprising the steps of:

suturing a first sheet having a smooth bottom surface and a loop top surface to the first edge of the incision with said smooth bottom surface facing the interior organ and said loop top surface facing the incision;

suturing a second sheet having a hook bottom surface and a smooth top surface to the opposite edge of the incision with said hook bottom surface facing the interior organ and said smooth top surface facing the incision;

applying a slight pulling force on said first sheet and said second sheet for applying a minimal tension force between the first edge and the opposite edge;

mating said first sheet with said second sheet by impressing said loop top surface against said hook bottom surface for bridging a first gap of the incision and preventing an abdominal compartment syndrome illness and reducing infection risks;

awaiting a decompression of the abdominal hypertension for reducing the enlarged abdominal volume of the abdominal organs and the protrusion of the abdominal organs through the abdominal incision; and joining the first edge and an opposite edge for closing the abdominal incision.

2. A process for bridging a gap of an abdominal incision as set forth in claim 1, wherein the step of awaiting a decompression of the enlarged abdominal volume for reducing the protrusion of the abdominal organs through the abdominal incision further including the step of:

disengaging said second sheet from said first sheet by lifting said loop top surface from said hook bottom surface for exposing the gap of the abdominal incision;

trimming said first sheet for reducing the area of said smooth bottom surface and said loop top surface;

trimming said second sheet for reducing the area of said hook bottom surface and said smooth top surface;

applying a slight pulling force on said first sheet and said second sheet for applying a minimal tension force between the first edge and the opposite edge;

mating said first sheet with said second sheet by impressing said loop top surface against said hook bottom surface for bridging a second gap of the incision and preventing an abdominal compartment syndrome illness and reducing infection risks; and awaiting a second decompression of the abdominal hypertension for reducing the enlarged abdominal volume of the abdominal organs and the protrusion of the abdominal organs through the abdominal incision.

* * * * *